United States Patent [19]

Sengstock

[11] Patent Number: 5,497,542
[45] Date of Patent: Mar. 12, 1996

[54] METHOD OF ASSEMBLING AN INNER TUBE INTO AN OUTER TUBE

[75] Inventor: Robert H. Sengstock, Kaukauna, Wis.

[73] Assignee: Kimberly-Clark Corporation, Neenah, Wis.

[21] Appl. No.: 395,748

[22] Filed: Feb. 28, 1995

Related U.S. Application Data

[62] Division of Ser. No. 174,119, Dec. 27, 1993, abandoned.

[51] Int. Cl.$^6$ .................................................. B23P 11/00
[52] U.S. Cl. ............................. 29/464; 29/434; 29/282; 29/281.1
[58] Field of Search .................................. 29/434, 455.1, 29/464, 281.1, 281.5, 771, 777, 282, 234; 269/21; 53/252, 258, 585; 493/379; 28/118–120

[56] References Cited

U.S. PATENT DOCUMENTS

| | | | |
|---|---|---|---|
| 654,564 | 7/1900 | Dargatz. | |
| 716,040 | 12/1902 | Holt. | |
| 1,224,735 | 5/1917 | Gamache, Jr. et al. | |
| 1,908,403 | 5/1933 | Budde. | |
| 2,386,590 | 10/1945 | Calhoun | 128/285 |
| 2,444,528 | 7/1948 | Popper et al. | 128/285 |
| 2,495,420 | 1/1950 | Popper et al. | 18/5 |
| 2,596,811 | 5/1952 | Carlson | 88/24 |
| 2,690,598 | 10/1954 | Bletzinger et al. | 19/144.5 |
| 2,704,068 | 3/1955 | Beranek | 128/127 |
| 2,879,770 | 3/1959 | Graham, Jr. | 128/263 |
| 3,033,298 | 5/1962 | Johnson | 175/209 |
| 3,063,453 | 11/1962 | Brecht | 128/285 |
| 3,124,134 | 3/1964 | Gardner | 128/263 |
| 3,372,695 | 3/1968 | Beliveau et al. | 128/1 |
| 3,465,390 | 9/1969 | Mooney | 19/144.5 |
| 3,558,093 | 1/1971 | Bok | 248/362 |
| 3,606,643 | 9/1971 | Mooney | 19/144.5 |
| 3,643,661 | 2/1972 | Crockford | 128/263 |
| 3,699,962 | 10/1972 | Hanke | 128/263 |
| 3,765,416 | 10/1973 | Werner et al. | 128/263 |
| 3,765,417 | 10/1973 | Crockford | 128/263 |
| 3,807,399 | 4/1974 | Morman et al. | 128/263 |
| 3,835,856 | 9/1974 | Warncke | 128/263 |
| 3,874,031 | 4/1975 | Simon | 19/144.5 |
| 3,946,463 | 3/1976 | Warncke et al. | 19/144.5 |
| 3,971,378 | 7/1976 | Krantz | 128/285 |
| 4,006,515 | 2/1977 | Mast, Jr. | 19/144.5 |
| 4,012,809 | 3/1977 | Warncke et al. | 19/144.5 |
| 4,067,087 | 1/1978 | Mast, Jr. | 28/118 |

(List continued on next page.)

FOREIGN PATENT DOCUMENTS

| | | |
|---|---|---|
| 719081 | 10/1965 | Canada. |
| 0544057A1 | 6/1993 | European Pat. Off.. |
| 96307 | 3/1898 | Germany. |
| 241771 | 12/1911 | Germany. |
| 423181 | 12/1925 | Germany. |
| 2260940 | 12/1972 | Germany. |
| 0594580 | 11/1947 | United Kingdom. |
| 0603282 | 6/1948 | United Kingdom. |
| 1469972 | 4/1977 | United Kingdom. |
| WO84/04667 | 6/1984 | WIPO. |

Primary Examiner—S. Thomas Hughes
Attorney, Agent, or Firm—Thomas J. Connelly

[57] ABSTRACT

An apparatus and method of assembling an inner tube into a hollow outer tube is disclosed for forming a tampon applicator. The apparatus includes a first member configured to mate with the outer tube and a second member configured to mate with the inner tube. A vacuum is intermittently supplied to the first and second members to hold the inner and outer tubes in coaxial alignment. The apparatus also includes a push rod which is designed to contact and move the inner tube off of the second member and into the outer tube. The movement of the push rod is activated by a control mechanism which can reciprocally move the push rod a predetermined distance at a set time to permit the inner tube to be inserted into the outer tube. The control mechanism also enables the push rod to be separated from the inner tube after the two tubes are assembled. The method includes the sequential steps involved in using a vacuum to position the inner and outer tubes in coaxial alignment and then using the push rod to insert the inner tube into the outer tube.

7 Claims, 5 Drawing Sheets

U.S. PATENT DOCUMENTS

| | | | |
|---|---|---|---|
| 4,108,299 | 8/1978 | Mast, Jr. | 28/119 |
| 4,250,798 | 2/1981 | Yamato et al. | 53/585 X |
| 4,269,187 | 5/1981 | Sakurai et al. | 128/263 |
| 4,276,881 | 7/1981 | Lilaonitkul | 128/263 |
| 4,332,251 | 6/1982 | Thompson | 128/263 |
| 4,361,150 | 11/1982 | Voss | 128/263 |
| 4,411,647 | 10/1983 | Sakurai et al. | 604/16 |
| 4,412,833 | 11/1983 | Wiegner et al. | 604/14 |
| 4,424,054 | 1/1984 | Conn et al. | 604/11 |
| 4,536,178 | 8/1985 | Lichstein et al. | 604/15 |
| 4,543,086 | 9/1985 | Johnson | 604/11 |
| 4,676,773 | 6/1987 | Sheldon | 604/16 |
| 5,061,274 | 10/1991 | Kensey | 606/213 |
| 5,141,212 | 8/1992 | Beeding | 269/21 |
| 5,153,971 | 10/1992 | Van Iten | 28/118 |
| 5,158,535 | 10/1992 | Paul et al. | 604/15 |
| 5,364,083 | 11/1994 | Ross et al. | 269/21 |

METHOD OF ASSEMBLING AN INNER TUBE INTO AN OUTER TUBE

This is a divisional application of application Ser. No. 08/174,119, filed on Dec. 27, 1993, now abandoned.

FIELD OF THE INVENTION

This invention relates to an apparatus and method of assembling an inner tube into an outer tube to form a tampon applicator.

BACKGROUND OF THE INVENTION

Tampon applicators are used to assist a woman in positioning a catamenial tampon into her vagina. Tampon applicators come in a variety of shapes and configurations. Many tampon applicators utilize two members telescopically assembled, wherein the first member is designed to contain a tampon and the second member is designed to expel the tampon from the first member. The first member or outer tube usually consists of a hollow tubular barrel connected to a smaller fingergrip portion having an opening formed therethrough. The second member or inner tube can be in the form of a solid stick or a hollow tube sized to slide within the opening formed in the fingergrip portion. The inner tube is designed to expel the tampon from the outer tube when pushed into the outer tube. Essentially all tampon applicators sold today have a straight, longitudinal central axis.

The apparatus and method of assembling an inner tube into the outer tube is fairly simple when both members have a straight, central axis. However, when both members have an arcuately shaped longitudinal central axis or when the radius of curvature of each longitudinal central axis is different, it becomes difficult to assemble the two members. The assembly is further complicated when the inner tube has an outer diameter which is just slightly less than the size of the opening formed in the fingergrip portion of the outer tube. Lastly, when the assembly is conducted at very fast line speeds, the task takes on enormous proportions. Up until now, no one has had to assemble two arcuately shaped hollow tubes at very high line speeds.

Now an apparatus and method have been developed which enables an inner tube to be assembled into a hollow outer tube to form a tampon applicator.

SUMMARY OF THE INVENTION

Briefly, this invention relates to an apparatus and method of assembling an inner tube into a hollow outer tube to form a tampon applicator. The apparatus includes a first member configured to mate with the outer tube and a second member configured to mate with the inner tube. A vacuum is intermittently supplied to the first and second members to hold the inner and outer tubes in coaxial alignment along an arcuate centerline. The apparatus also includes a push rod which is designed to contact and move the inner tube off of the second member and into the outer tube. The movement of the push rod is controlled by a mechanism which can reciprocally move the push rod a predetermined distance at a set time to permit the inner tube to be inserted into the outer tube.

The method includes the sequential steps involved in using a vacuum to position the inner and outer tubes in alignment to one another and then using the push rod to insert the inner tube into the outer tube.

The general object of this invention is to provide an apparatus and a method for assembling an inner tube into an outer tube to form a tampon applicator. A more specific object of this invention is to provide an apparatus for inserting an arcuately shaped inner tube into a hollow, arcuately shaped outer tube.

Another object of this invention is to provide an apparatus for coaxially aligning a hollow, arcuately shaped inner tube into a hollow, arcuately shaped outer tube.

A further object of this invention is to provide a quick and efficient method of inserting an inner tube into a hollow outer tube at very fast line speeds.

Still another object of this invention is to provide an inexpensive method of inserting an inner tube into a hollow outer tube.

Still further, an object of this invention is to provide an apparatus and method which can assemble an inner tube into a hollow outer tube at machine speeds in excess of 100 assemblies per minute.

Other objects and advantages of the present invention will become more apparent to those skilled in the art in view of the following description and the accompanying drawings.

DETAILED DESCRIPTION OF THE PREFERRED EMBODIMENT

Figure 1:
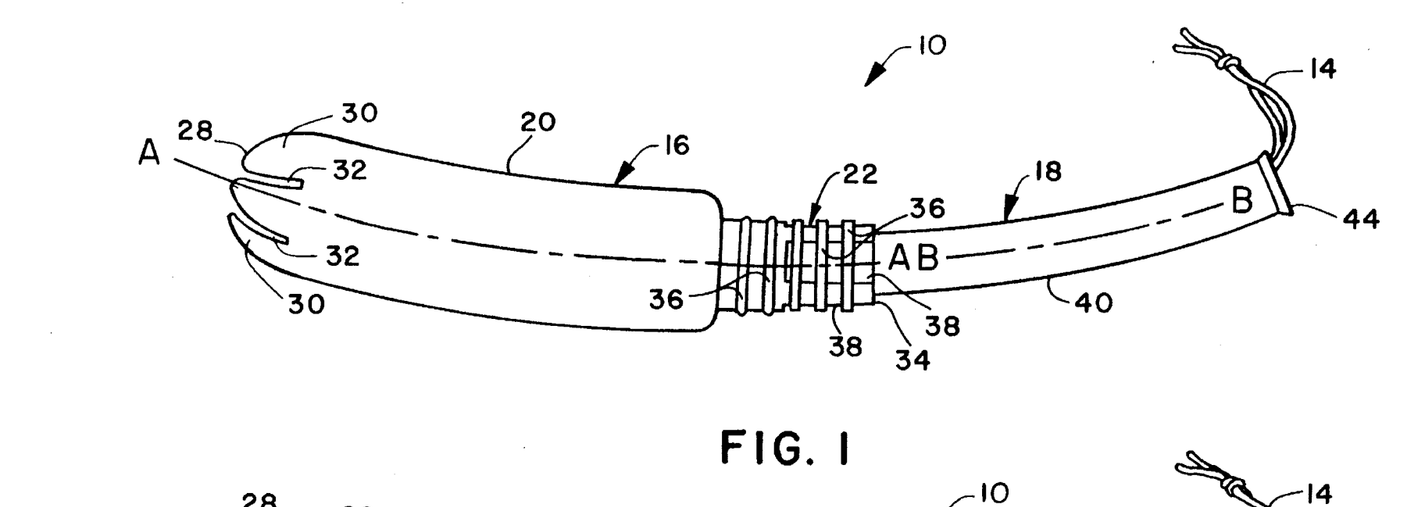
FIG. 1 is a side elevational view of a curved tampon applicator for facilitating insertion of an absorbent tampon into a woman's vagina.
Figure 2:
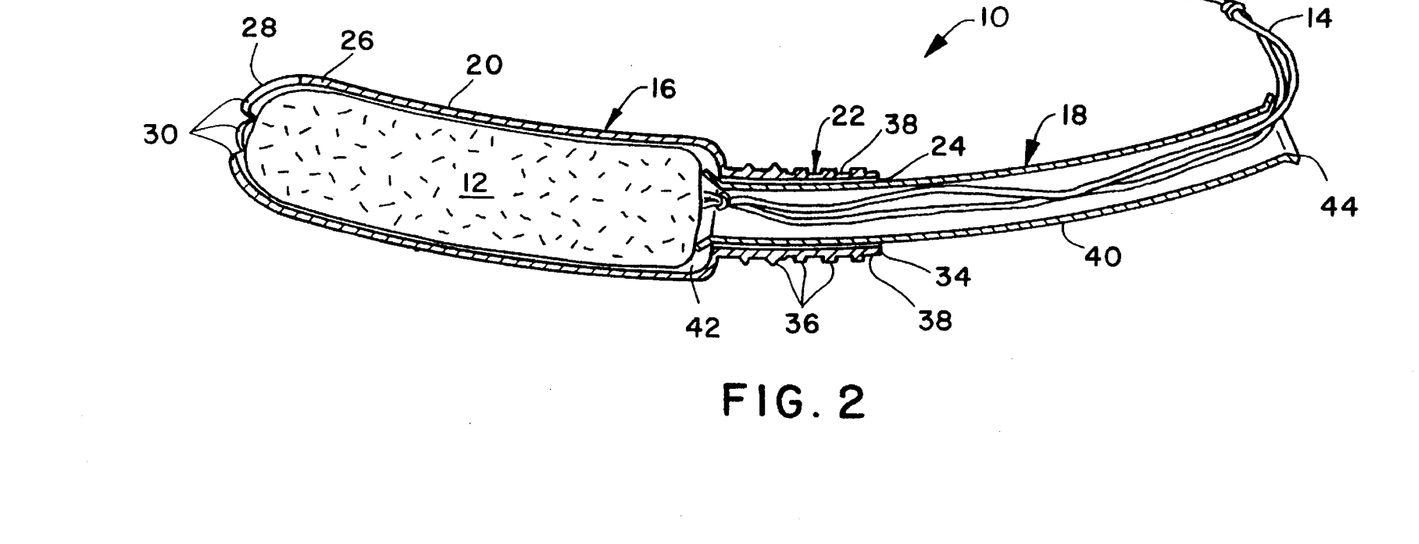
FIG. 2 cross-sectional view of the curved tampon applicator shown in FIG. 1 depicting the tampon contained in the barrel of the outer tube.

Referring to FIGS. 1 and 2, a curved tampon applicator 10 is shown containing a catamenial tampon 12. The catamenial tampon 12 has a withdrawal string 14 attached to an end thereof. The tampon 12 is intended to be inserted into a woman's vagina during her menstrual period to block the flow of menstrual fluid, blood, etc. therefrom. The withdrawal string 14 provides an easy means for the woman to remove the tampon 12 after it has absorbed a given quantity of body fluid.

The curved tampon applicator 10 includes an outer tube 16 and an inner tube 18. The outer tube 16 can be constructed from paper, cardboard, plastic, etc. The outer tube 16 is hollow in configuration and has an arcuate shape with a longitudinal centerline A—A formed on an arc having a predetermined radius of curvature. The arc can be formed on a radius of curvature of between about 6 to 10 inches, preferably between about 7 and 9 inches, and most preferably, about 8 inches. An arc having a certain radius of curvature is equivalent to an arcuate segment of a circle having a given radius. The outer tube 16 has a stepped outer configuration with an enlarged barrel 20, designed to contain the absorbent tampon 12, connected to a smaller fingergrip portion 22. The fingergrip portion 22 has an opening 24 formed therethrough which is sized and shaped to receive the inner tube 18. Preferably the opening 24 has an elliptical, oval, square or rectangular cross-sectional configuration.

The enlarged barrel 20 of the outer tube 16 has a generally circular or round cross-sectional shape and is sized to be just slightly larger than the outside diameter of the absorbent tampon 12, which it is designed to retain. The enlarged barrel 20 has a wall 26 and a forward end 28 through which the tampon 12 is expelled. The wall 26 is relatively thin and preferably has a smooth outer periphery. The wall 26 tapers in thickness as it approaches the forward end 28 of the outer tube 16. The difference in wall thickness is beneficial in that it permits petals 30 to be formed approximate the forward end 28. The petals 30 are thin, flexible members separated by slots or grooves 32. The petals 30 are capable of bending radially outward as the absorbent tampon 12 is expelled from the tampon applicator 10. A plurality of petals 30, preferably an odd number, such as 3, 5, 7 etc., should be utilized.

The fingergrip portion 22 of the outer tube 16 contains a wall 34 which can have a smooth outer periphery. The wall 34 is a structural member which should be somewhat thicker than the wall 26 of the barrel 20. When the wall 34 is relatively thick, it will prevent the inner tube 18 from rotating within the opening 24 because the wall 34 will not give or be capable of easily becoming distorted. By properly orienting the inner tube 18 in the opening $2_¢$, one can be assured that the inner tube 18 will properly expel the tampon 12 from the outer tube 16. The fingergrip portion 22 also contains one or more circular rings or ribs 36 formed about its exterior circumference. The circular rings 36 provide a gripping surface to assist the user in holding the curved tampon applicator 10 between her thumb and middle finger. Her index finger is used to push the inner tube 18 into the outer tube 16 and thereby expel the absorbent tampon 12. The fingergrip portion 22 can also have one or more pairs of flat surfaces 38, formed in its exterior surface so as to make it easier for a woman to grasp and hold the tampon applicator 10. Other known types of gripping means can also be used.

The inner tube 18 can be solid or hollow or it can be solid with a hollow cavity form at one end. The inner tube 18 can be constructed from paper, cardboard, plastic, etc. The hollow configuration is preferred. The inner tube 18 has an arcuate shape with a longitudinal centerline B—B formed on an arc having a predetermined radius of curvature. The arc can be formed on a radius of curvature of between about 6 to about 10 inches, preferably between about 7 to about 9 inches, and most preferably, about 8 inches. An arc having a certain radius of curvature is equivalent to an arcuate segment of a circle having a given radius. The radius of curvature of the inner tube 18 can be equal to, less than or greater than the radius of curvature of the outer tube 16. The inner tube 18 has a wall 40 which preferably has a smooth outer periphery and a uniform cross-sectional configuration. The exterior periphery of the wall 40 is sized and configured to mate with and be slidable in the opening 24 of the fingergrip portion 22. An elliptical, oval, square or rectangular cross-sectional shape is desirable. It permits the inner tube 18 and the outer tube 16 to move in a telescoping fashion while preventing the inner tube 18 from rotating relative to the outer tube 16. The inner tube 18 has first and second spaced apart ends 42 and 44, see FIG. 2, which can be flared after assembly with the outer tube 16. The flared ends will prevent the inner tube 18 from being physically separated from the outer tube 16.

Additional information relating to the curved tampon applicator 10 is taught in U.S. Pat. No. 5,158,535 issued to Paul et al. on Oct. 27, 1992. This patent is incorporated by reference and made a part hereof.

Figure 3:
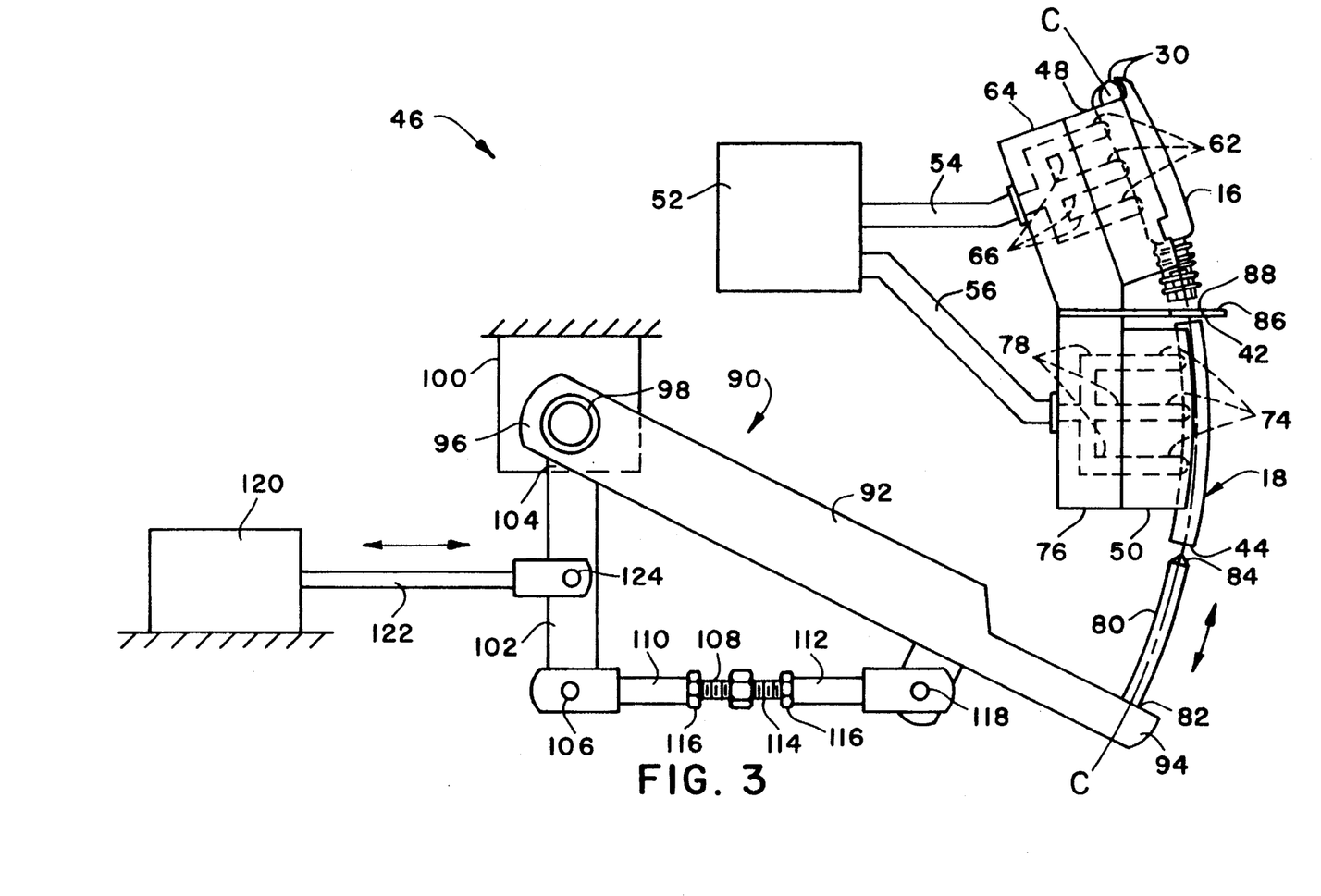
FIG. 3 is a schematic diagram of an apparatus for assembling an inner tube into a hollow outer tube.

Referring to FIG. 3, an apparatus 46 is shown for assembling the inner tube 18 into the hollow outer tube 16. The apparatus 46 includes a first member 48 configured to mate with at least a portion of the smooth outer periphery of the outer tube 16 and a second member 50 configured to mate with at least a portion of the smooth outer periphery of the inner tube 18. The first and second. members 48 and 50 are connected to a source of vacuum 52 by hoses 54 and 56, respectively. The source of vacuum 52 is capable of supplying a predetermined amount of vacuum to the first and second members, 48 and 50 respectively, so that they are capable of holding the outer and the inner tube, 16 and 18 respectively, in coaxial alignment to one another. Preferably, the vacuum is intermittently supplied to the first and second members, 48 and 50 respectively. By intermittent it is meant that the vacuum can be started and stopped at set intervals.

Figure 4:
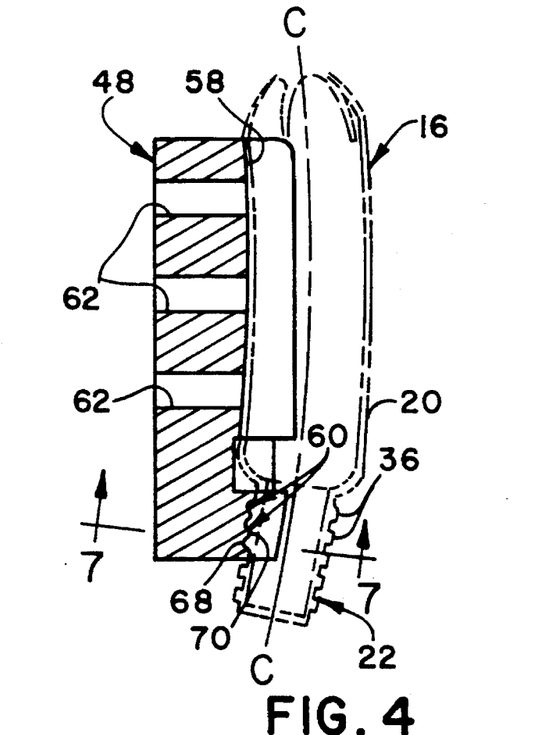
FIG. 4 is side elevational view of the first member holding the outer tube in a vertical arrangement.
Figure 5:
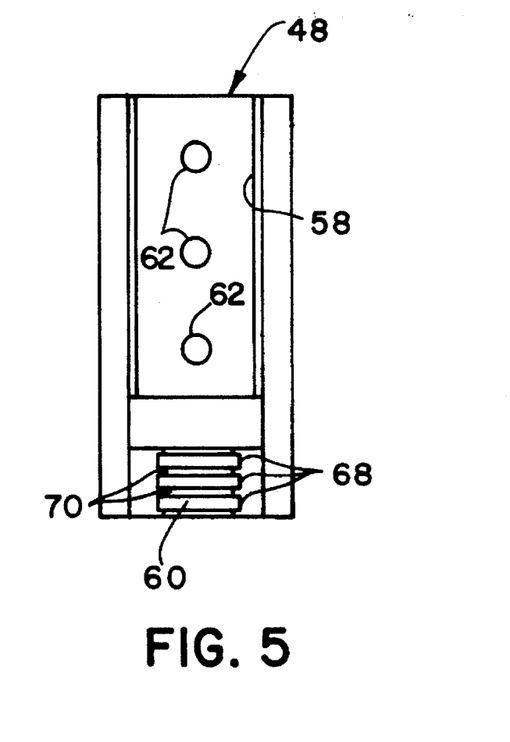
FIG. 5 is a right front view of the first member shown in FIG. 4.
Figure 7:
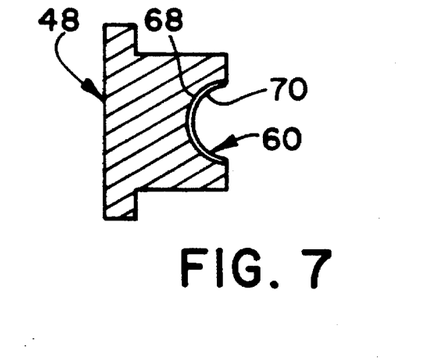
FIG. 7 is a cross-sectional view of the first member shown in FIG. 4 taken along line 7—7.

The outer tube 16 is preferably positioned vertical above the inner tube 18 on an arcuately shaped, longitudinal central axis C—C. A vacuum of about 10 inches of mercury at the source of vacuum 52 works well in a setup where the vacuum is distributed to a plurality of individual first and second members, 48 and 50 respectively, which are arranged on a rotary turret. The vacuum present at each first member 48 may be about 5 inches of mercury. This drop in vacuum is created by the distance each first member 48 is located away from the source of vacuum 52, the various diameters of the hoses 54 and 56, vacuum leakage in the system, etc. Referring to FIGS. 4 and 7, the first member 48 includes first and second elongated pockets, 58 and 60 respectively, which are axially aligned along the arcuate centerline C—C and configured to fit the contour of the barrel 20 and the fingergrip portion 22, respectively, of the outer tube 16. The first member 48 has one or more passageways 62 formed therein. Three passageways 62 are shown in FIGS. 3–5, which connect the first pocket 58 to the source of vacuum 52. The actual connection, best illustrated in FIG. 3, includes a mounting block 64 to which the hose 54 is attached. Within the mounting block 64 are one or more passageways 66 which line up with the passageways 62 formed in the first member 48. The first member 48 is secured to the mounting block 64 by machine screws or other types of fasteners known to those skilled in the art.

Figure 6:
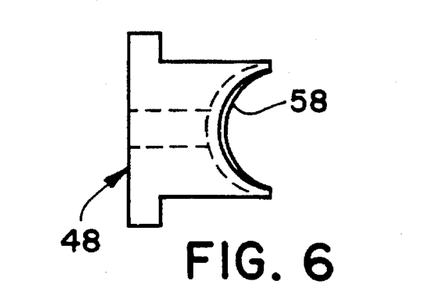
FIG. 6 is a top view of the first member shown in FIG. 4.

Referring again to FIGS. 4–7, the first pocket 58 formed in the first member 48 is semi-circular in cross-section and elongated in shape, see FIG. 6. The first pocket 58 is sized to mate with and snugly fit the contour of the barrel 20. This snug fit allows the vacuum in the passageways 62 to form a seal with the outer periphery of the barrel 20 and hold it stationary relative to the first member 48. The second pocket 60 formed in the first member 48 is sized and shaped to fit the contour of the fingergrip portion 22. The second pocket 60 is elongated in shape. However, since no vacuum is applied to the second pocket 60, there is no need for a snug fit. Formed perpendicular to the longitudinal axis of the elongated second pocket 60 are one or more semi-circular grooves 68, each of which are sized to accept and retain a portion of one of the circular rings 36 formed in the fingergrip portion 22, see FIGS. 4, 5 and 7. Each groove 68 has at least one side wall or shoulder 70. Preferably, each groove 68 has a pair of side walls or shoulders 70. The purpose of the semi-circular groove 68 and adjacent side walls 70 is to hold the outer tube 16 stationary against linear forces which could be applied to it. Vacuum is weak in shear and the outer tube 16 could easily be slid out of the first pocket 58 if it was not for the semi-circular groove 68. In the embodiment shown in FIG. 5, three semi-circular grooves 68 are shown with adjacent side walls 70.

Figure 8:
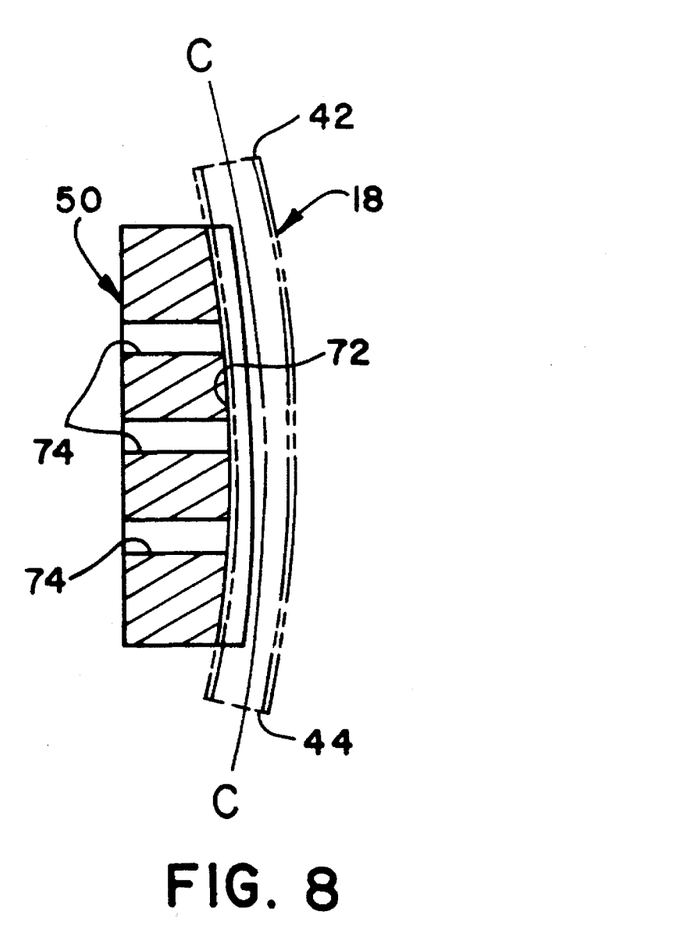
FIG. 8 is a side elevational view of the second member holding the inner tube in a vertical arrangement.
Figure 9:
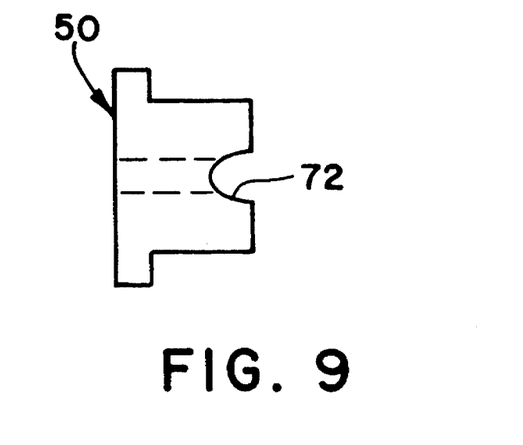
FIG. 9 is a bottom view of the second member shown in FIG. 8.

Referring to FIGS. 8 and 9, the second member 50 includes a first elongated pocket 72 formed on the arcuate shaped, longitudinal central axis C—C. The pocket 72 is configured to fit the contour of the inner tube 18. The second member 50 has one or more passageways 74 formed therein. Three passageways 74 are present in FIG. 8. It should be noted that the number of passageways, 66 and 74 respectively, formed in the first and second members, 48 and 50 respectively, can vary depending upon the size and shape of the part being held by vacuum, the pressure of the vacuum, the material each part is constructed of, etc. The passageways 74 connect the pocket 72 to the source of vacuum 52. The actual connection, best illustrated in FIG. 3, includes a mounting block 76 to which the hose 56 is attached. Within the mounting block 76 are one or more passageways 78 which line up with the passageways 74 formed in the second member 50. The second member 50 is secured to the mounting block 76 by machine screws or other types of fasteners known to those skilled in the art.

Referring again to FIG. 3, the apparatus 46 further includes a movable push rod 80 having first and second spaced apart ends, 82 and 84 respectively. The push rod 80 is an elongated member formed on the arcuately shaped, longitudinal central axis C—C. The second end 84 of the push rod 80 is conical shaped so as to enable it to enter into the hollow end of the inner tube 18. The conical shaped end 84 is sized so that a portion of the cone is too large to enter the opening in the inner tube 18 and therefore will contact the wall 40 and be capable of moving the inner tube 18 upward toward the outer tube 16. The conical shaped end 84 is designed to contact and preferably enter an end of the inner tube 18. To assist in aligning the first end 42 of the inner tube 18 with the opening 24 in the outer tube 16, a guide plate 86 having an aperture 88 formed therethrough can be used. The guide plate 86 is situated between the first member 48 and the second member 50 and is affixed in a stationary position. The aperture 88 is sized and configured to guide the first end 42 of the inner tube 18 into the opening 24 formed in the fingergrip portion 22.

As depicted in FIG. 3, the conical end 84 of the push rod 80 enters the lower end 44 of the inner tube 18 and moves the inner tube 18 upward. In this process, the inner tube 18 is slid along the elongated pocket 72 since vacuum is weak in shear. As the inner tube 18 is moved upward, its upper end 42 will align with, and enter the opening 24 formed in the fingergrip portion 22 of the outer tube 16. The frictional resistance between the two tubes, 16 and 18 respectively, will cause the outer tube 16 to want to move linearly upward. This linear force caused by the frictional engagement of the two tubes, 16 and 18 respectively, can be high enough to break the vacuum seal between the outer tube 16 and the first elongated pocket 58. However, the physical interference between the groove 68 and the adjacent side walls 70 with one or more of the circular rings 36 is sufficient to prevent the outer tube 16 from being moved linearly out of the pockets 58 and 60. Therefore, the outer tube 16 will be retained in the first and second pockets 58 and 60 formed in the first member 48. The apparatus 46 further includes a control mechanism 90 for reciprocally moving the push rod 80 a predetermined distance at a set time. Since the next step in the assembly process requires that the inner tube 18 extend out of each end of the outer tube 16, it is desirable to move the inner tube 18 a sufficient distance to accomplish this. The inner tube 18 has a defined length which is slightly longer than the outer tube 16. This means that the inner tube 18 is capable of extending out of each end of the outer tube 16. It should be noted that this is not a necessary feature for all tampon applicators 10 and that the amount the inner tube 18 is moved by the push rod 80 can be varied.

The control mechanism 90 includes a pusher arm 92 having a first end 94 into which the first end 82 of the push rod 80 is affixed and a second end 96 pivotally attached to a shaft 98. The shaft 98 is held secure to a stationary block 100. A connecting arm 102 having a first end 104 and a second end 106 is pivotally attached at the first end 104 to the shaft 98 and is pivotally attached at the second end 106 to a turnbuckle 108. The turnbuckle 108 is a metal coupling consisting of two oblong members 110 and 112 internally threaded at both ends and into which a threaded rod 114 is screwed. A nut 116 is threaded on the rod 114 and serves to lock the turnbuckle 108 at a given length. The turnbuckle 108 provides a fine adjustment for the control mechanism 90 in that it will determine the distance the conical end 84 of the push rod 80 is spaced from the lower end 44 of the inner tube 18. One end of the oblong member 110 is pivotally attached to the second end 106 of the connecting arm 102 and the distal end of the other oblong member 112 is pivotally attached to the pusher arm 92 at a point 118 located intermediate the first and second ends, 94 and 96 respectively, of the pusher arm 92.

The control mechanism 90 further includes a cam mechanism 120 having a linkage arm 122 which is pivotally attached to the connecting arm 102 at a point 124 located intermediate its first and second ends, 104 and 106 respectively. Movement of the cam mechanism 120 will cause the linkage arm 122 to move the connecting arm 102 to the right or left with corresponding movement being imputed into pusher arm 92 via the turnbuckle 108. This in turn will cause the push rod 80 to move upward or downward along the arcuate centerline C—C. It should be noted that the cam mechanism 120 could be replaced with a hydraulic or pneumatic cylinder, an electrical motor, or other type of mechanical, hydraulic, electrical, or electro-mechanical device familiar to those skilled in the art for accomplishing an identical function.

METHOD

Figure 10:
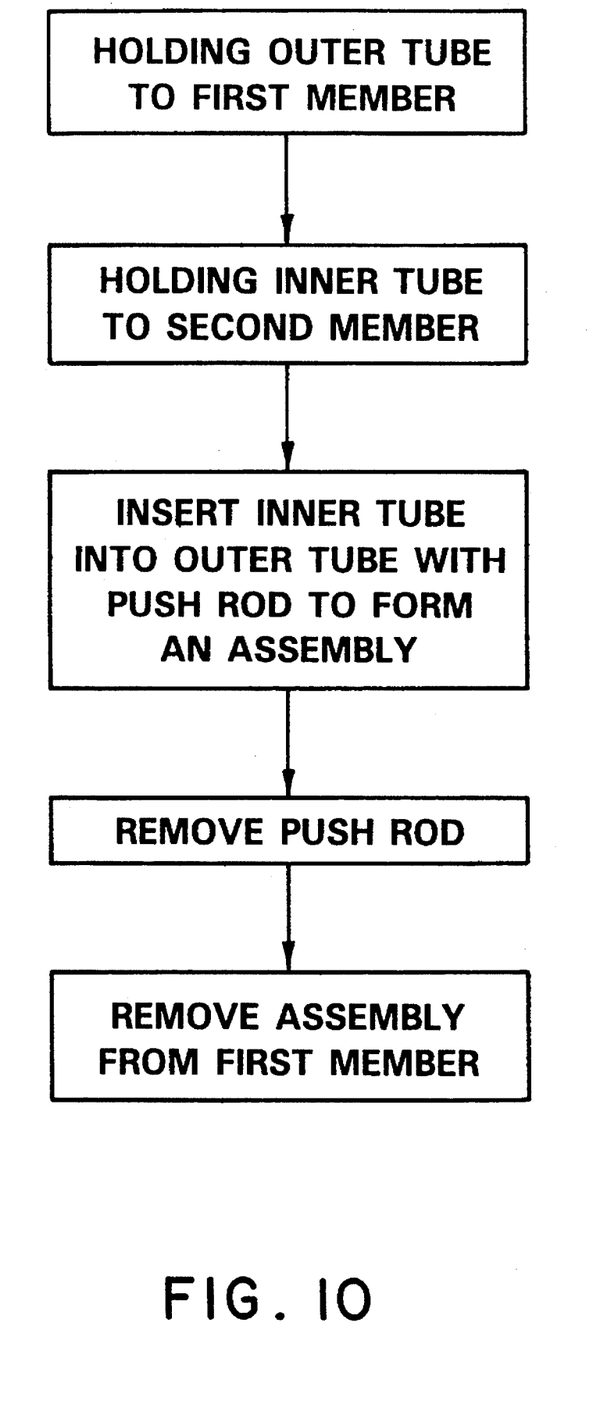
FIG. 10 is a flow diagram of the method of assembling an inner tube into a hollow outer tube.

Referring to FIG. 10, the method of assembling the inner tube 18 into the outer tube 16 to form a tampon applicator 10 is as follows. The source of vacuum 52 is activated to supply a vacuum through the hose 54 and the passageways 62 and 66 so that a vacuum is present at the first member 48. Likewise, a vacuum is created in the hose 56 and the passageways 74 and 78 so that a vacuum is present in the second member 50. An outer tube 16 is then placed in the pockets 58 and 60 of the first member 48 and is held in the desired position by the vacuum. An inner tube 18 is then placed in the pocket 72 of the second member 50. In this position, the inner tube 18 is coaxially aligned along an arcuate centerline with the opening 24 formed in the fingergrip portion 22 of the outer tube 16.

The control mechanism 90 is then activated to move the push rod 80 along the arcuate, central axis C—C and upward into contact with the lower end 44 of the inner tube 18. The conical end 84 of the push rod 80 will enter the lower end 44 of the inner tube 18 and push the inner tube 18 upward so that the upper end 42 enters into the opening 24. The inner tube 18 can be slid off the pocket 72 formed in the second member 50 even though a vacuum is present because the vacuum is weak in shear. This allows the inner tube 18 to slide along the pocket 72 at a constant speed matching the movement of the push rod 80. The initial insertion of the inner tube 18 into the outer tube 16 will create frictional resistance between the wall 34 of the fingergrip portion 22 and the wall 40 of the inner tube 18. This frictional resistance will result in a linear force being exerted on the outer tube 16 which will try to dislodge the outer tube 16 from the pockets 58 and 60 of the first member 48. However, the outer tube 16 will not be dislodged because the groove 68 and its adjacent side walls 70 will physically retain the circular ring 36 which is formed on the fingergrip portion 22. The push rod 80 will travel a predetermined distance at least equal to the length of the inner tube 18. This will assure that the inner tube 18 is completely inserted into the outer tube 16 to form an assembly. Preferably, the push rod 80 will traverse a distance greater than the length of the inner tube 18. This will enable the second end 44 of the inner tube 16 to be flush with the bottom of the outer tube 16 and allow the assembly to be removed from the first member 48. It should be noted that the inner tube 18 has to completely pass through the guide plate 86 so as to permit it to be cleanly removed from the first member 48.

After the inner tube 18 is inserted into the outer tube 16, the push rod 80 is withdrawn by the control mechanism 90. The vacuum is then removed from the first member 48 and from the second member 50 and the assembly is removed from the first member 48. It should be noted that the vacuum can be intermittently supplied to the first and second members, 48 and 50 respectively, in which case, the vacuum can be simultaneously removed from both members 48 and 50. Alternatively, the vacuum can be constantly routed to the second member 50 but be intermittently supplied to the first member 48. This is possible because the vacuum does not have to be turned off in order to remove the inner tube 18 from the pocket 72 of the second member 50.

The above apparatus 46 and method are capable of producing assemblies very quickly and in a cost efficient manner. Normal operating speeds can easily produce in excess of 100 assemblies per minute. Top speed can produce about 500 assemblies per minute. The actual number of assemblies produced in a given time period will be dependent upon a number of factors, including the size of the finished assembly, the material of which the tubes are made of, the number of vacuum pockets available to receive the individual tube members, the machine speed, down stream processes, etc.

While the invention has been described in conjunction with a specific embodiment, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

I claim:

1. A method of assembling an inner tube into a hollow outer tube, said method comprising the steps of:
    a) placing said outer tube onto a first member which is connected to a source of vacuum and supplying a vacuum to retain said outer tube in a desired position;
    b) placing said inner tube onto a second member which is connected to a source of vacuum and supplying a vacuum to hold said inner tube in coaxial alignment with said outer tube;
    c) using a push rod to insert said inner tube into said outer tube to form an assembly;
    d) withdrawing said push rod from said inner tube; and
    e) removing said vacuum from said first member to allow said assembly to be removed.

2. The method of claim 1 further comprising moving said push rod along an arcuate central axis.

3. The method of claim 1 wherein said push rod is moved a distance at least equal to the length of said inner tube.

4. The method of claim 1 wherein said vacuum is intermittently supplied to both said first and second members.

5. The method of claim 1 wherein said vacuum is simultaneously removed from said first and second members.

6. The method of claim 1 wherein said inner tube is slid linearly off of said second member by said push rod while said vacuum is applied.

7. A method of assembling a hollow inner tube into a hollow outer tube to form a tampon applicator, said method comprising the steps of:
    a) placing said outer tube onto a first member which is connected to a source of vacuum and supplying a vacuum to retain said outer tube in a desired position;
    b) placing said inner tube onto a second member which is connected to a source of vacuum and supplying a vacuum to hold said inner tube in coaxial alignment with said outer tube;,
    c) using an arcuately shaped push rod to insert said inner tube into said outer tube to form an assembly;
    d) moving said push rod away from said inner tube; and
    e) overcoming said vacuum applied to said first member to allow said assembly to be moved.

\* \* \* \* \*